United States Patent [19]

Chappell

[11] 4,144,881

[45] Mar. 20, 1979

[54] APPAREL WORN FOR THE AID AND PROTECTION OF THE BODY AND FOR THE SUPPORT AND ASSISTANCE OF IMPAIRED JOINT FUNCTION

[76] Inventor: Cluff E. Chappell, 2121 Valencia, NE., Albuquerque, N. Mex. 87110

[21] Appl. No.: 803,865

[22] Filed: Jun. 6, 1977

[51] Int. Cl.² .............................................. A61F 3/00
[52] U.S. Cl. ................................. 128/80 R; 128/80 F
[58] Field of Search ................. 128/80 R, 80 F, 80 C, 128/88, 87 R

[56] References Cited

U.S. PATENT DOCUMENTS

| 1,336,695 | 4/1920 | Gromes | 128/88 |
| 3,902,482 | 9/1975 | Taylor | 128/80 F |
| 4,064,874 | 12/1977 | Valin | 128/80 C |

*Primary Examiner*—John D. Yasko
*Attorney, Agent, or Firm*—Walter R. Keller

[57] ABSTRACT

An orthopedic prosthetic device, formed of interlocking links, which allows for full motion in the plan of articulation, yet which resists, lateral forces applied to the joint, and tendencies of the joint to dislocate in a lateral direction. The interlocking links having adjustable stops so that motion in the plane of articulation may be restricted if desired.

4 Claims, 11 Drawing Figures

APPAREL WORN FOR THE AID AND PROTECTION OF THE BODY AND FOR THE SUPPORT AND ASSISTANCE OF IMPAIRED JOINT FUNCTION

BACKGROUND

Field of Art

This invention relates generally to orthopedic support prosthesis and more particularly to mechanical joints and supports for ankles, elbows, knees, and wrists, and the like. Active persons such as runners, football players, soccer players and skiers as well as ordinary citizens frequently suffer injuries to a variety of joints. Knee, ankle, wrist, elbow, and neck dislocation and sprains are common. Once injured a joint may suffer lasting residual effects and subject the injured person to a chronic condition in which the joint may dislocate, or sprain again when placed under unusual stress. Such a condition frequently requires the injured person to use some sort of protective device when unusual stresses are anticipated such as participation in athletic events. Indeed, a restriction of normal movement is frequently part of the treatment of an injured joint. Such a protective prothesis device can limit movement of the injured joint permitting more rapid healing and recovery.

Previous devices have usually used pivoted hinged frameworks, or devices which attach as their free ends to bands or cuffs, or are inserted into an elastic sleeve. While such devices may provide some lateral support the amount of lateral support is a function primarily of the rigidity of the device and especially the design of the pivot and pivot pin. Furthermore, prior art does not provide a convenient means whereby the degree of allowable movement in the plane of articulation may be adjusted or controlled.

VALIN, U.S. Pat. No. 4,064,874 described a knee joint support device having articulated lateral supports. The degree of rigidity of VALIN'S device is limited by the surface area of matching tongue portions and the size of the flat head rivets. Furthermore, VALIN does not provide any means for controlling, limiting or restricting motion in the plane of articulation of the joint.

It is an objective of the present invention to provide a supporting device for joints which is highly resistive to lateral forces and movements, and provides a means for controlling or restricting movement in the plane of articulation.

SUMMARY

The invention is a brace member having a base, and a plurality of crescent shaped discs, and an end piece. The base has a convex semi-circular end with a T-shaped groove. The first crescent shaped disc has a T-shaped tongue on its concave side, as do all other discs, which slideably fits into the T-shaped groove on the base. The first crescent shaped disc has a T-shaped groove on its convex side, as do all other discs, which slideably accepts the T-shaped tongue of the second crescent shaped disc. Any desired number of crescent shaped discs can be interlocked, chain fashion, to achieve the desired length of the brace. The end piece has a concave semi-circular surface which is a T-shaped tongue, and which slideably interconnects to the last crescent shaped disc. The geometry of T-shaped, semi-circular tongue and groove interlockings, and the geometry of a rigid arc between interlocking discs, combined with the increased contacting surface area between crescent shaped discs provides substantially improved resistance to lateral forces and movement of the joint.

The base member, and each crescent shaped disc, are provided with stop blocks which slide into the T-shaped groove. The stop blocks have a set screw which is screwed into the base of the T-shaped groove wedging the stop block in the T-shaped groove. Thus by properly adjusting the stop blocks in the base member and the crescent shaped discs, the movement in the plane of articulation can be limited or restricted, even can be eliminated.

The invention in various sized, utilizing any convenient attaching device such as a brace bar, cuffs, or elastic sleeve can obviously be used on ankles, wrists, elbows, knees, and could be adapted for use with the neck or torso of a person.

DESCRIPTION OF PREFERRED EMBODIMENT

Figure 1:
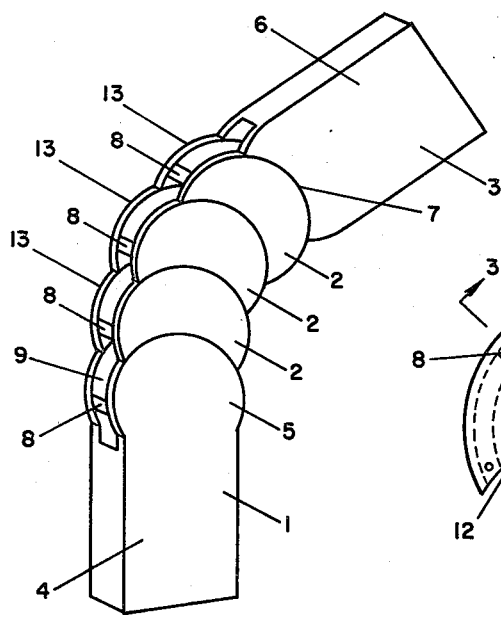
FIG. 1 is an isometric view of the invention.

Refering to the drawings, FIG. 1 shows the invention to consist of a base member 1, a plurality of crescent shaped disc 2, and an end piece 3.

The base member 1 is generally flat, and has a rectangular attaching end 4 and a convex semi-circular end 5 whose radius is approximately equal to the width of the attaching end 4. The attaching end 4 can be equipped with any convenient means of attaching to a bar, cuff or straps as desired such as but not limited to slots or rivet holes. If the invention is to be inserted into a pocket in an elastic sleeve, the attaching end 4 need only be smoothed and without corners to prevent chafing of the wearer, or snagging and tearing the elastic sleeve. The semi-circular end 5 of the base member 1 is shown to have a T-shaped groove 9 in the edge.

The crescent shaped discs 2, are generally flat and all identical. Each crescent shaped disc 2 has a concave edge 12 and a convex edge 13. The concave edge 12 has a cross-sectional shaped in the form of a T-tongue 14, which is sized to slideably fit the T-shaped groove 9. The convex edge 13 has a cross-section of a T-shaped groove 9. The convex edge 13 and concave edge 12 of the crescent discs 2 are circular arcs whose radius is approximately equal to the radius of the semi-circular end of the base member 1.

The end piece 3 is generally flat, and is shown to have a rectangular attaching end 6 which is generally the same shape as the attaching end 4 of the base member 1. The means of attaching the invention in an elastic sleeve to which it is applied to the wearer's body or joint is not critical of the invention and in fact will vary with application. It is recognized that the means for attaching base member 1 to the wearer's joint or body need not be the same as the means for attaching the end piece 3 to the wearer. The end piece 3 also has a concave end 7 which is semi-circular in shape whose radius is approximately equal to the radius of the semi-circular end 5 of the base member 1. The concave end 7 has a cross-section of a T-shaped tongue 14 which slideably fits in the T-shaped grooved 9 on either the crescent shaped discs 2 or the base member 1.

In use, the T-shaped tongue 14 of the first crescent shaped disc 3 is slid into T-shaped groove 9 of the base member. Additional crescent shaped discs 2 are successively slideably mated to the preceding crescent shaped disc 2. When the desired length of the invention has been achieved, the end piece 3 is finally mated to the last crescent shaped disc 2.

Figure 2:
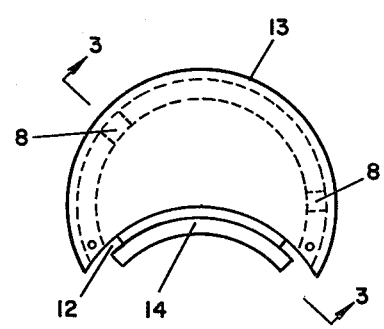
FIG. 2 is a plan view of a crescent shaped disc.
Figure 3:
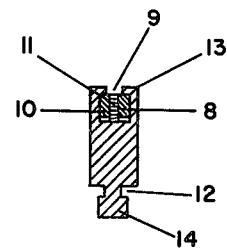
FIG. 3 is a sectional view of a crescent shaped disc cut on 3—3 of FIG. 2.

FIGS. 2 & 3 shows the invention to have a plurality of stop-blocks 8, each having a threaded tap 10, and a set screw 11. The stop-blocks 8 are shaped to loosely but slideably fit the T-shaped groove 9 on base member 1 and each crescent shaped disc 2. The set screw 11 is threaded to fit the threads of the threaded tap 10. The threaded tap 10 is located approximately in the center of the stop-block 8 and passes through it. In practice, the stop-block 8 is slid into the T-shaped groove 9 to the desired location. The set screw 11, having already been partially screwed into the threaded tap 10, is further screwed through the threaded tap 10 so that it presses against the bottom of the T-shaped groove 9, until the stop-block 8 is forced against the outer lips of the T-shaped groove 9; thus securely holding the stop-block 8 into position. In assembly of the invention, a first stop-block 8 is enserted in the manner just described; then the slideably mating part either a crescent shaped disc 25; or the end piece 3, as appropriate is slideably mated; then a second stop-block 8 is inserted in the manner described; thus limiting the movement of the slideably mated part in the plane of articulation to the desired degree.

Figure 4:
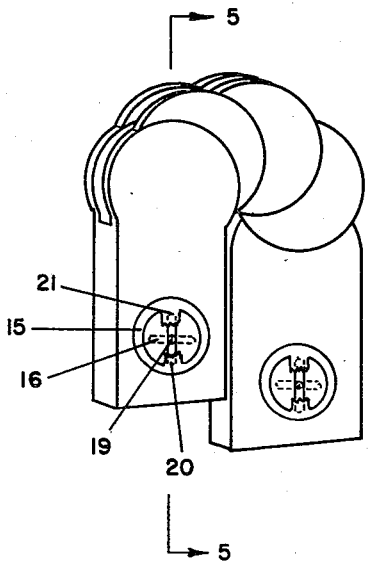
FIG. 4 is an isometric view of the invention with attachment means.
Figure 5:
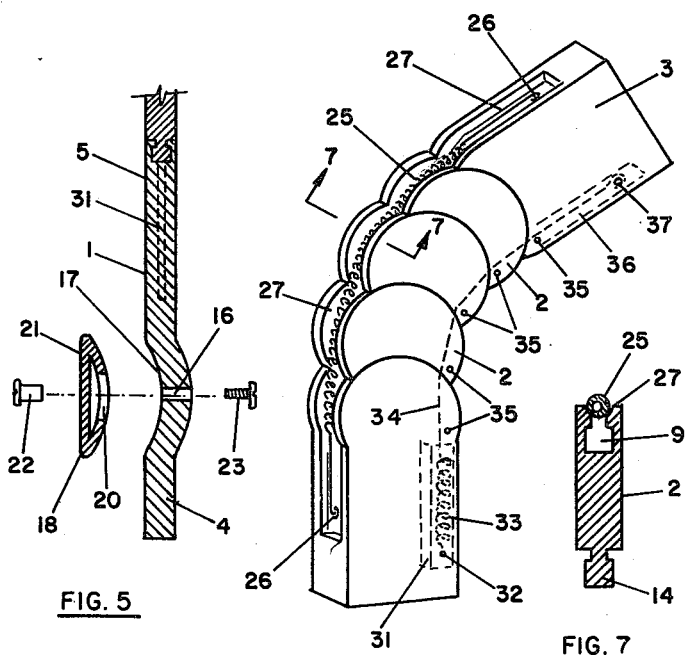
FIG. 5 is a partial sectional of the base member cut on 5—5 of FIG. 4.

Refering now to FIGS. 4 and 5, a means for adjustably fastening the invention to a cuff or other means for attaching to the wearer's body is shown. Generally speaking, the wearer's limb is of different size on either side of his joint, for example a condition as a heavy muscular thigh above the joint and a smaller thinner calf below the knee joint. A proper fit above and below a joint with the invention on either side of the joint will splay the invention. This can cause chaffing, and binding of the invention. Thus the base member 1 and the end piece 3 may be modified to have an attaching means generally shown as 15. The attaching means comprises a slot 16, a hollow 17, a cup 18, and a pin 19. The base member 1 or end piece 3 or both, on a circumferential diameter of the hollow 17 normal to the length to the invention is a slot 16. The cup 18 is spherical in shape having a similar cup slot designate 20. The cup 18 also has a bar 21 across its lips. The pin 19 consists of a flat headed nut 22 and a flat screw 23 which is threaded to screw into the flat headed nut. The pin 19 is sized to slideably fit through slot 16 and cup slot 20. The invention is then assembled and loosely attached to the wearer, and the cup 18 and hollow 17 mate is a manner similar to a ball joint. Upon achieving a proper fit, the pin 19 is tightened by screwing the flat screw 23 in to flat headed nut 22, and providing a friction lock. It is recognized and within the scope of the invention that the cup 18 could be made as a part of a special brace or bar for a foot support, wrist support or other body adapter and assembled to the present invention.

Figure 6:
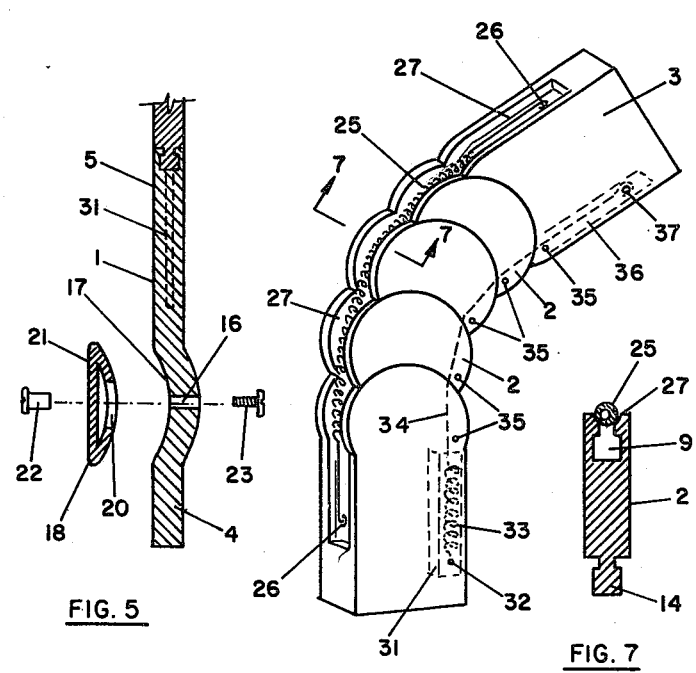
FIG. 6 is an isometric view of the invention with means for aiding joint dysfunction by spring energizing.
Figure 7:
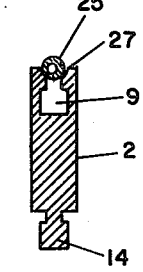
FIG. 7 is a partial sectional view of a crescent shaped disc cut on 7—7 of FIG. 6.
Figure 8:
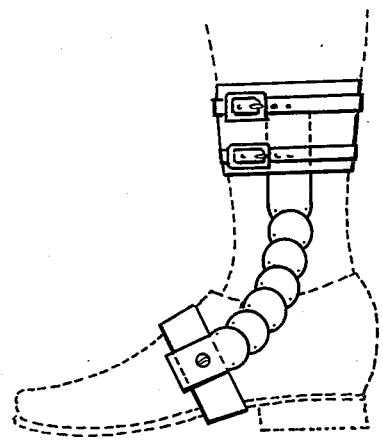
FIG. 8 is an illustration of the application of the invention on an ankle of the wearer.

FIGS. 6 and 7 show the invention thus fare described, adapted with a means for aiding joint dysfunction. Certain injuries, paralysis, and other conditions can leave the afflicted person with little or no capability to move a joint in one direction or both. FIG. 6 shows the invention to be adapted with a recess 31, a spring 33, a wire 34, a plurality of pins 35, and a wire attachment 37. The recess 31 is a hollowed out portion of the base member 1 having a spring attachment 37 therein which may be any convenient means for attaching the spring 33. The spring 33 is a coil having its other end attached to a wire 34. The base member 1, and the crescent shaped discs have openings on one edge. The pins through the base member 1, the plurality of crescent shaped discs 2, and end piece 3, provide guides for the wire 34 which is threaded through the openings into the wire attachment 37 in the end piece 3. The wire attachment 37 may be any convenient means of securely attaching the wire 34 to the end piece 3, and is shown as a recess having a bar onto which the wire is attached. In assembling the invention and fitting to the wearer, the spring 33 and wire 34 are put in tension by adjusting the length of the wire 34.

The aforedescribed means for aiding joint dysfunction, once installed and fitted would be more or less permanent and the wearer would be practically unable to dislodge or disengage the tension mechanism. FIGS. 6 and 7 also shows the invention adapted, for an easily removable aid for joint dysfunction, being a spring 25, two spring fasteners 26, and a channel 27. The spring fasteners 26 are made a part of the end piece 3, and base member 1, on each edge thereof, and are to functionally attach the end of spring 25 thereto. The channel 27 is sized to accomodate the spring 25. The channel 27 consists of a shaping of the end piece 3, base member 1, and the ends of the crescent shaped disc 2 to provide a channel 27 in which spring 25 may lie. Spring 25 is attached at one end to a fastner 26 on the base member 1, and under tension to the fastener 26 on the end piece 3 so that the spring 25 lays in the channel 27. An other spring 25 may be similarly attached on the other edge of the invention. As desired two, or only one spring 25 may be used; and it is obvious that the spring 25 means can be used to return the limb of the wearer to a position the wearer may not physically be able to achieve, or it may be used to apply a resistive force against movement, thus requiring the wearer to exert a greater force to move and thus provide an exercising requirment to the weakened muscles of the wearer.

It is envisioned that all parts of the invention would be made of spring steel, but any suitable material such as rigid durable plastic would be satisfactory. The rigidity of the invention is to some degree controlled by the tolerances in the mating T-shaped groove 9 and T-shaped tongue 14. However, the present invention provides three points of contact between mating discs when lateral bending forces are applied.

The two ends and the center of the T-shaped tongue 14 press against the T-shaped groove 9, creating a bending in each crescent shaped disc 2 from end to end as well as bending from the concave edge 12 to the convex edge 13. Thus, the lateral forces is resisted by a plurality of internal stresses in the crescent shaped disc, instead of simple bending in pivotal links. Additionally, it is important to realized that the invention provides full movement in the plane of articulation if desired. As shown in FIG. 4 the end piece 3 can be moved all the way so that it is adjacent to the base member 1, and application of the invention to a joint of the wearer restricts lateral movement, but not necessarily movement in the plane of articulation.

Figure 9:
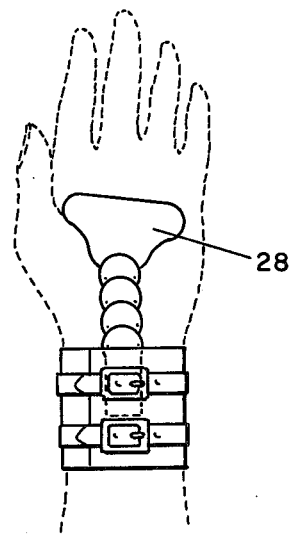
FIG. 9 is an illustration of the application of an invention on the palm side of the wrist of the wearer.
Figure 10:
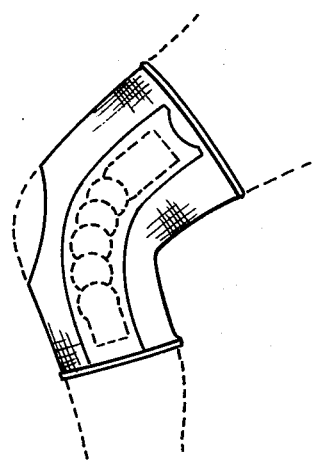
FIG. 10 is an illustration of the application of the invention on the knee of the wearer.
Figure 11:
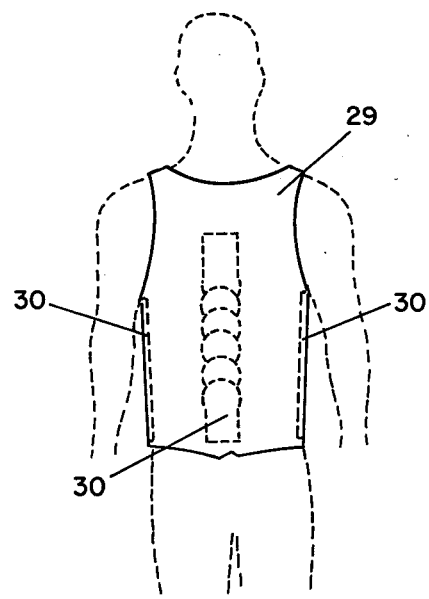
FIG. 11 is an illustration of the application of the invention of the thorax of the wearer.

FIGS. 8, 9, 10, and 11 shows the application of the invention to various parts of the human body, namely the ankle, wrist, knee, and thorax respectively. Application to the hips could be accomplished by attaching to the waist and thighs of the wearer. FIG. 9 shows a cuff type on a wrist, with a palm rest 28 shaped to conveniently fit the palm. FIG. 11 shows a vest 29 type on the thorax with pocket inserts 30 down the spine and under each arm. On the thorax, a single pocket insert of the invention in the vest down the spine would restrict back bending frontward and rearward but allow side to side movement. By placing the invention in a pocket insert under each arm, side to side movement is restricted.

I claim:

1. A protective orthopedic prosthetic device comprises:
    a means for attaching the device to the limb or body of the wearer,
    a base member being generally flat having an attaching end which attaches or is inserted into the means for attaching the device to the body of the wearer, and the base member having a convex semi-circular end whose edge has a T-shaped groove,
    a plurality identical of crescent shaped discs having a convex edge whose cross-section is a T-shaped groove identical to the T-shaped groove of the base member, and each crescent shaped disc having a concave edge whose cross section is a T-shaped tongue which is sized to slideably fit the T-shaped groove of the base member and other crescent shaped discs; the concave edge and the convex edge of the crescent shaped discs being circular arcs whose radii are both approximately equal to the radius of the semi-circular end of the base member;
    and an end piece being generally flat having an attaching end which attaches or is inserted into the means for attaching the device to the limb or body of the wearer, and having a concave semi-circular end whose cross section is a T-shaped tongue which is sized to slideably mate and fit the T-shaped groove in the crescent shaped disc and the T-shaped groove in the base member, the radius of the concave semi-circular end of the end piece being approximately equal to the radius of the semi-circular end of the base member,
    and a plurality of stop blocks, being two for each T-shaped groove, each step-block having a threaded tap at its approximate center said threaded tap passing clear through the stop-block, the stop-block being sized to loosely slideably fit the T-shaped groove in the base member and crescent shaped discs,
    and a plurality of threaded set screws to screw into and through the threaded taps,
    and an optional means for aiding joint dysfunction.

2. The device of claim 1 wherein the means for attaching the device to the limb of wearer comprises:
    a hollow in the base member or end piece or both
    a slot in the hollow
    a cup, having an attaching bar
    a cup slot
    and a threaded flat heat nut and a matching threaded flat head screw sized to slideably fit through the cup slot and slot in the hollow, assembled so as to provide a ball joint type mechanism and a friction locking means.

3. The device of claim 1 wherein the means for aiding joint dysfunction comprises:
    a recess in the base member having a spring attachment
    a coil spring attached on one end to the spring attachment,
    a wire attached to the other end of the coil spring
    a plurality of openings in the base member, of the plurality of crescent shaped discs, and the end piece,
    a plurality of pins in each opening to guide the wire,
    and a wire attachment in the end piece, to which the wire, after being threaded through the openings, is attached.

4. The device of claim 1 wherein the means for aiding joint dysfunction comprises:
    two channels formed on the edges of the invention by forming the edges of the base member, end piece and each liner,
    four spring fasteners, one on each edge of the base member, and one on each edge of the end piece;
    a spring which is attached at one end to the fastener on one edge of the base member, and at the other end to the fastner on the corresponding edge of the end piece; said springs being in tension when so attached; and laying in the aforesaid channels.

* * * * *